US012622995B2

(12) United States Patent
Fusi et al.

(10) Patent No.: US 12,622,995 B2
(45) Date of Patent: May 12, 2026

(54) AIR SANITATION DEVICE BY EMISSION OF A BARRIER OF ULTRAVIOLET RADIATION IN AN AIR FLOW

(71) Applicants:Consiglio Nazionale Delle Ricerche, Rome (IT); UNIVERSITA' DEGLI STUDI DI FIRENZE, Florence (IT)

(72) Inventors: Franco Fusi, Florence (IT); Giovanni Romano, Florence (IT); Guido Toci, Rome (IT); Barbara Patrizi, Rome (IT)

(73) Assignees: CONSIGLIO NAZIONALE DELLE RICERCHE, Rome (IT); UNIVERSITA' DEGLI STUDI DI FIRENZE, Florence (IT)

( * ) Notice: Subject to any disclaimer, the term of this patent is extended or adjusted under 35 U.S.C. 154(b) by 341 days.

(21) Appl. No.: 18/270,547

(22) PCT Filed: Dec. 30, 2021

(86) PCT No.: PCT/IB2021/062460
§ 371 (c)(1),
(2) Date: Jun. 30, 2023

(87) PCT Pub. No.: WO2022/144821
PCT Pub. Date: Jul. 7, 2022

(65) Prior Publication Data
US 2024/0293593 A1 Sep. 5, 2024

(30) Foreign Application Priority Data
Dec. 31, 2020 (IT) ........................ 102020000032918

(51) Int. Cl.
*A61L 9/20* (2006.01)

(52) U.S. Cl.
CPC ............ *A61L 9/20* (2013.01); *A61L 2209/111* (2013.01); *A61L 2209/12* (2013.01)

(58) Field of Classification Search
None
See application file for complete search history.

(56) References Cited

U.S. PATENT DOCUMENTS 10,987,440 B1 * 4/2021 Sood ........................ A61L 2/10
2003/0190254 A1 * 10/2003 Falat .................... A61C 1/0076
422/4

(Continued)

FOREIGN PATENT DOCUMENTS

CA 3 090 973 10/2020
KR 10-2011 0031810 3/2011

(Continued)

OTHER PUBLICATIONS

International Search Report dated Apr. 25, 2022 issued in PCT International Patent Application No. PCT/IB2021/062460, 3 pp.

*Primary Examiner* — Andrew Smyth
(74) *Attorney, Agent, or Firm* — NIXON & VANDERHYE P.C.

(57) ABSTRACT
A device for air sanitation in circumscribed environments generates a sterilising barrier substantially consisting of superimposing a descending vertical laminar air flow and a peripherally delimited ultraviolet radiation beam also directed downwards. The device, of simplified design and small size, comprises structure for delivering a vertical laminar air flow at a controlled and humidified temperature, as well as, adjacent to such delivery structure, one or more sources for the external emission of an ultraviolet radiation beam of a wavelength appropriately chosen to offer a high germicidal action and not constitute a risk for humans. Therefore, such a substantially superimposed air flow and ultraviolet radiation beam form a barrier with high sterilising
(Continued)

power and capable of generating confined areas. The device thus conceived is suitable for installation in circumscribed environments, typically crowded, in which the transmission of pathogens and, consequently, the risk of contagion is to be reduced. It is particularly applicable in public places such as offices, restaurants, public establishments of various kinds as well as transport.

9 Claims, 2 Drawing Sheets

(56)                    References Cited

U.S. PATENT DOCUMENTS

| | | | |
|---|---|---|---|
| 2012/0199003 A1 | 8/2012 | Melikov et al. | |
| 2020/0030469 A1 | 1/2020 | Neister et al. | |
| 2021/0353794 A1* | 11/2021 | Popa-Simil | A61L 2/10 |
| 2021/0386885 A1* | 12/2021 | Ismail | A61L 2/10 |
| 2022/0008575 A1* | 1/2022 | Sood | A61L 2/10 |

FOREIGN PATENT DOCUMENTS

| | | | | |
|---|---|---|---|---|
| KR | 20110031810 A | * | 3/2011 | A61L 9/20 |
| KR | 10-2011-0052006 | | 5/2011 | |
| KR | 10-2012-0140413 | | 12/2012 | |
| KR | 10-2013-0034192 | | 4/2013 | |

* cited by examiner

AIR SANITATION DEVICE BY EMISSION OF A BARRIER OF ULTRAVIOLET RADIATION IN AN AIR FLOW

This application is the U.S. national phase of International Application No. PCT/IB2021/062460 filed Dec. 30, 2021 which designated the U.S. and claims priority to IT 102020000032918 filed Dec. 31, 2020, the entire contents of each of which are hereby incorporated by reference.

TECHNICAL SECTOR

The present invention relates to the technical field of germicidal equipment for air sanitation and disinfection.

In particular, the invention relates to a device for sanitising air by generating an ultraviolet radiation barrier in air flow.

BACKGROUND ART

The limited environments where human activities are carried out or where, in general, there is high anthropogenic concentration, such as offices, waiting rooms, restaurants, public transport, etc., can generate ideal conditions for the multiplication and propagation of pathogens. In such circumstances, the air can act as a vector of such pathogens and, consequently, as a means of transmitting infectious disease conditions.

In fact, as is known, there is a close correlation between air quality in confined spaces and the health of the individuals who occupy them. As an example, Sick Building Syndrome identifies a pathological condition associated with poor ventilation and, in general, reduced air quality indoors; moreover, according to estimates by the European Centre for Disease Prevention and Control, between 15,000 and 70,000 deaths are recorded each year in Europe due to influenza A and B viruses alone, which are mainly transmitted by air.

According to recent literature, the transmission of viral and/or bacterial infections by air is induced by the propagation of microscopic particles, emitted in the form of aerosols by breathing, coughing or sneezing, of variable size in the order of micrometres. In particular, due to the small size of most of the particles constituting such aerosols, which can reach diameters of even less than 1 μm, their residence in air can last for several hours.

Notoriously, pathogens such as bacteria, viruses, fungi, etc. can be deactivated by exposure to UV radiation. In this respect, the equipment typically used for sanitising environments uses UV lamps which emit radiation at a wavelength of around 254 nm, of which, however, the danger to man has been demonstrated.

As an alternative to the widely and commonly used germicidal UV lamps mentioned above, in order to reduce the risk for humans, there has recently been the diffusion of excimer lamps, or sources of narrow-band UV radiation produced by the spontaneous emission of unstable molecular complexes in the excited state (i.e., excimers), mainly consisting of dimers of noble gases or a halogen atom bound to a noble gas atom. In the field of environmental sanitation, in addition to high efficiency and intensity, these devices offer the emission of far UV wavelength radiation, whose non-hazardous nature has been ascertained for humans. In particular, the lamps made for this purpose, carrying out their antimicrobial action by means of light emission at a wavelength equal to 222 nm or 175 nm, allow their use in populated environments. In this context, document US2020030469A1 reports a device for sterilising air and surfaces consisting of an excimer lamp at 222 nm, which is even proposed to be applied to the epidermis to obtain the rapid disinfection thereof. Currently, however, such lamps have spread mostly for the implementation of lighting systems, it follows that they do not provide a photon density per aerial volume such as to ensure the sanitation of entire environments.

A system for air sanitation in confined spaces, based on its disinfection by generation of a UV ray curtain is reported in document KR20130034192. The system described offers a solution for sanitising passage areas of normally crowded environments, and comprises a fixed frame inside which a UV lamp is positioned which generates an ultraviolet radiation curtain intended to reduce or minimise the penetration of pathogens from the outside. Such a system, although it prevents the spread of viruses and bacteria between communicating environments, cannot be used when the environments in question are populated, given the toxicity of radiation for humans. Furthermore, the system is inefficient because if the air rapidly passes through the UV barrier created by the device, the UV rays do not act on the passing air for a sufficient time to sanitise it.

Another system for air sanitation in confined environments comprising UV light sources is described in KR201100031810. In this system, a UV curtain is not created, but instead an air curtain previously sanitised by virtue of UV exposure is created through a blower. The blower is located inside a container body which has an air inlet opening at which there is a first source of UV rays and an air outlet opening at which there is a second UV source. The air outlet opening allows the air to escape which is pushed from the blower in a curtain air flow which introduces sanitised air into the environment and affects the people passing through it. In order to improve the sterilization efficiency, the UV radiation emitted by the second UV source is not confined in the container body but also exits the outlet opening so that it is irradiated to the region below the discharge port and it can directly hit a person passing below the discharge port. However, the UV radiation exiting the outlet opening does not form a collimated beam in a curtain but exits diffusely with a low concentration of UV rays. This is also evident from the fact that the outlet opening is partially closed by a grille element and the second source of UV rays is arranged inside the device between the blower and the aforesaid grille element which at least partially prevents the passage of air and UV rays. Thus, a curtain UV ray barrier is not generated in the device described in this document. In essence, the operating principle of this device is to sanitise the air which passes inside the device by exposing it to UV rays which are mainly confined in the housing of the device, and then reintroduce it into the sanitised environment. To improve the efficiency of the sterilization, the UV rays emitted by a second lamp located near the discharge port can partially pass through a grille of the discharge port to directly sterilize a person passing below the discharge port. Furthermore, as in the case of the previously discussed patent KR20130034192, the UV radiation emitted outside the device is potentially harmful to humans, whereby the device is not adapted to be used in the presence of people in the UV radiation diffusion zone outside the device. Another air curtain sanification device is disclosed in KR20110052006. In the document a device is disclosed that produces a curtain of sanitized air which has been sanitized through UV rays confined in a housing where air enters from an inlet port and is fed by a fan towards a discharge port to form in the outside a curtain of sanitized air.

As reported in document US2012199003A1, the diffusion of infectious biological agents in the environment can be reduced by means of a filtration/ventilation system which generates an upwards-directed air flow, and is mainly used for the construction of a partially isolated area around patients in healthcare-associated rooms. In this case, on the other hand, any pathogens are sucked upwards and not deactivated, it follows that the creation of this type of air shield does not coincide with the disinfection of the environment.

In general, the solutions of the known art do not offer air sanitation systems in confined environments, based on minimising the spread and inactivation of pathogens, which are compatible with the population conditions of the environments themselves.

SUMMARY OF THE INVENTION

In view of the foregoing, it is the object of the device according to the present invention to provide a solution for the disinfection and sanitation of air in confined spaces which can also operate in crowded conditions of the environment itself.

A further object of the invention is to propose a device which, although formed by easily available and low-cost units, ensures a high sterilising action.

Furthermore, it is the object of the invention to propose a device with a simplified design which allows an easy and immediate installation without requiring invasive interventions in the field of pre-existing architectures and furnishings.

A further object of the invention is to offer a versatile device, compatible with the incorporation of lamps of various kinds.

The objects listed, as well as other objects which will become apparent hereinafter, are achieved by means of an air sanitation device comprising a main body provided with one or more ultraviolet radiation emission lamps and means for forced air circulation, characterised in that the incorporated ultraviolet radiation emission lamps are such as to generate electromagnetic radiation in the range of wavelengths between 170 and 230 nm and are arranged so that the device emits a curtain electromagnetic radiation beam outwards, where the means for forced air circulation comprise channelling means such as to generate an outgoing curtain air flow also superimposed on or substantially adjacent to said electromagnetic radiation beam.

Thereby, the device performs its sanitation action by means of a two-dimensional ultraviolet radiation barrier associated with an air flow directed downwards, which by virtue of the peripheral confinement of the radiation and the chosen wavelengths lends itself to operation in commonly populated environments.

The main advantage offered by the device according to the invention is found in obtaining a high disinfection efficiency within a compact apparatus, which for this reason can be easily installed in small environments. In fact, the curtain air flow substantially coplanar with the UV curtain has a double function: it significantly increases the time of the air to be sanitised in the UV ray curtain which therefore have a greater time to exert their sanitation action; and reduces the probability that any viral particles are inhaled by the respiratory system by directing them towards the ground.

By way of example, the device according to the invention is suitable for use in waiting rooms or, in general, public premises, which wish to have a dividing element between adjacent stations. In fact, the UV barrier in air flow acts in such a sense as an element of confinement between neighbouring areas, consider the tables in refreshment areas or the seats in waiting rooms, so as to ensure the minimisation of the spread of infectious agents between adjacent locations and in fact increase the levels of safety in public spaces.

BRIEF DESCRIPTION OF THE DRAWINGS

These and other aspects and advantages of the invention will be comprehensible from the following description of a preferred embodiment of the invention and some of its variants, provided by way of non-exhaustive example, with the aid of the accompanying drawings, in which.

DETAILED DESCRIPTION OF PREFERRED EMBODIMENTS

Figure 2:
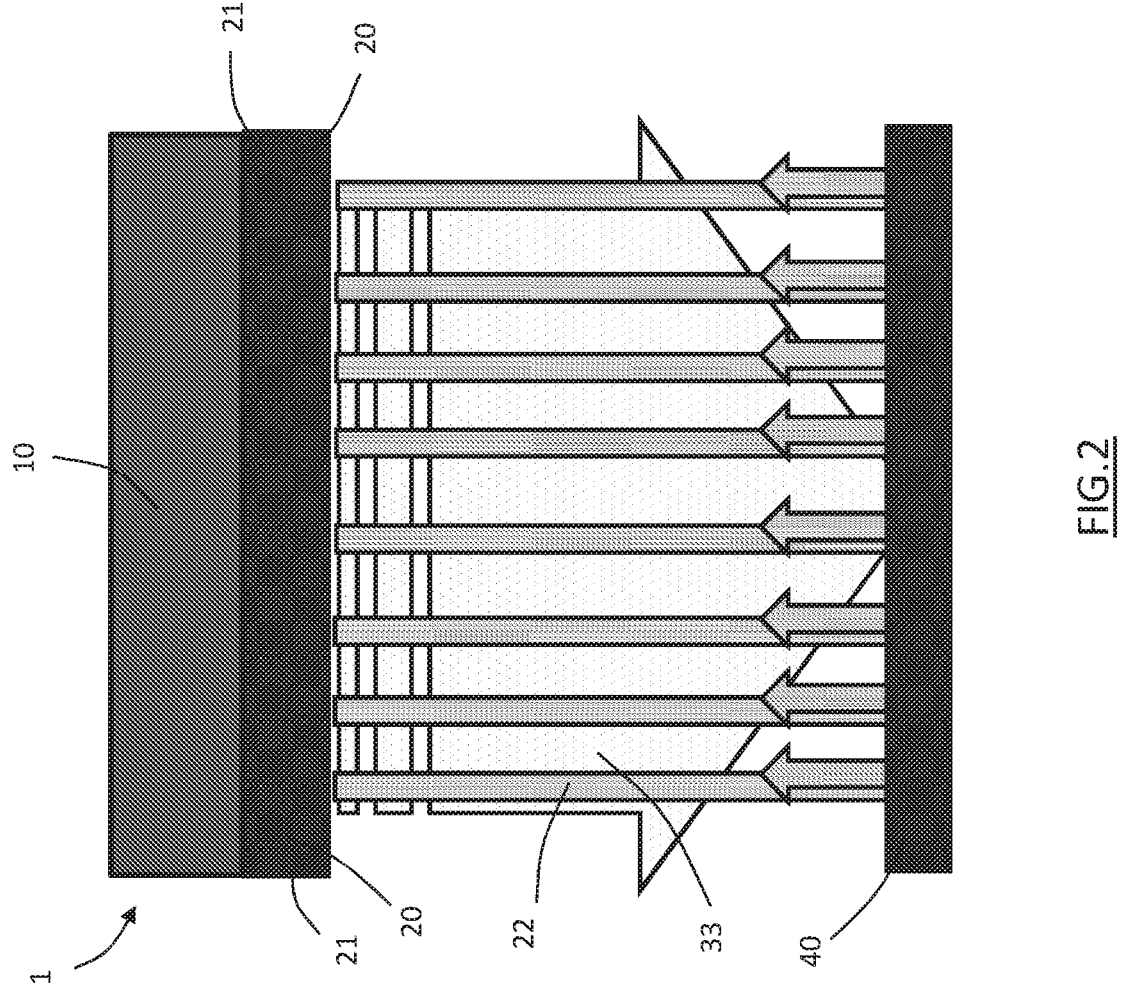
FIG. 2 shows a front view of the device of FIG. 1.
Figure 1:
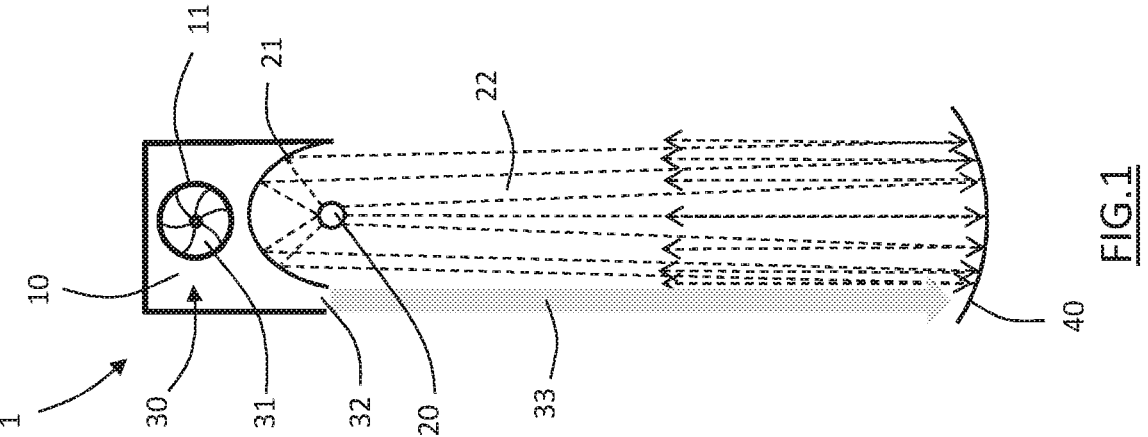
FIG. 1 shows a schematic side view of the air sanitation device by generation of an ultraviolet radiation barrier in air flow according to the invention.

Referring to FIGS. 1 and 2, a possible embodiment of the invention is shown, represented by a device with an overall elongated body indicated by 1.

The device 1 comprises a support frame constituting the main body, 10, which houses at least one UV radiation source, 20, and means for forced air circulation, 30.

The main body 10 includes two side walls, at the level of which at least one opening, 11, defining the air inlet, is formed. The forced air circulation means 30 are arranged at the opening 11, inside the main body 10, intended to direct the air flow inside the device. Preferably, they comprise a grille, for example of metallic type consisting of a plurality of slots, which can be placed in communication with a pre-chamber housing a filtration system. Such a filtration system (not shown) acts as the first element for reducing the infectious and polluting load of the inlet air. In fact, it can consist of high-efficiency particulate filters or, again, of any filter medium or device capable of adsorbing unwanted gases and particles.

In detail, the forced air circulation means 30 comprise ventilation means, 31, located inside the main body 10 near the air inlet, designed to suck the air inside the device. Advantageously, the ventilation means 31 are housed inside a silenced chamber. According to a preferred embodiment, said ventilation means 31 are centrifugal fans, this on the other hand not excluding the use of suction organs different than those shown, or the presence of attachment means for connecting the device to a compressed air circulation system or even the presence in the device of a compressed air container, since the presence of ventilation organs inside the device is not necessary in the latter two cases.

Additionally, the means for forced air circulation 30 include channelling means (not illustrated) which guide the gas flow inside the device. The latter can be made of different materials and define variable paths. By way of example, they can be made of metal, composite or thermoplastic materials and identify a labyrinth identified by appropriately oriented plates or also a spiral path. In any design and material they are made, their function is to put the air inlet area in communication with the outlet area.

It should be noted, in this sense, that such means for forced air circulation 30 are associated downstream with delivery means, 32, of the air itself, communicating with the outside and intended to supply the outlet air in a vertical laminar curtain-shaped air flow, 33, thus generating a gaseous curtain. In the case, for example, of a person sneezing near the device, the vertical laminar curtain-shaped air flow 33 will be hit by an aerosol flow which will disturb it for a few moments, mixing the vertical air blade with the aerosol particles, and giving the aerosol a vertical speed component, i.e., deviating it downwards. Thereby the aerosol flow will remain in the action volume of the UV rays for a longer time, thus greatly increasing the sanitation effectiveness of the device. It is clearly possible to use a wide variety of shapes and sizes of the delivery means 32. In the present case of a device with an elongated body, they are identified by a longitudinal opening extending along the length of the device itself.

Preferably, said air delivery means 32 are associated with outgoing flow rate control organs, adapted to adjust the supply speed of the gas flow so as to minimise the disturbance to the environment and reduce the risk of turbulence.

The device according to the invention also includes, associated with the air supply means 32, means for the control of temperature and hygrometry, such as electrical resistors and nebuliser nozzles (not shown), designed to increase the temperature of the outgoing air flow, simultaneously humidifying it. In addition, the latter can be envisaged combined with control means to enable said temperature and hygrometry control means to be operated and maintained at a distance. The effect of the association of the delivery means 32 with the means for the control of temperature and hygrometry is twofold, on the one hand the downwards movement of the gas flow is ensured due to the effect of the greater density of the particles, on the other hand the sanitation effect is enhanced, considering the known decay of the viral load at temperatures exceeding 25° C.

The main body 10 further houses one or more sources, 20, for emitting ultraviolet radiation of a wavelength between 170 and 230 nm, or radiation with a range of wavelengths with high germicidal power and reduced or no toxicity to humans, and which at the same time have a reduced interaction with the oxygen of the air so as not to produce or at most produce very limited amounts of ozone, as reported by multiple documents of the prior art. According to current technologies, advantageously usable sources are for example KrCl excimer lamps emitting in a narrow range around 222 nm or $Xe_2$ excimer lamps emitting in a range around 175 nm. Such sources 20 are located in the lower part of the central body 10, downstream of the channelling means and near the delivery means 32. In particular, they are mounted above the base of the main body 10. In the diagram shown, the ultraviolet radiation propagates directly outwards, generating an electromagnetic radiation curtain beam, 22, in a downwards direction; alternatively, the lower part of the main body 10 can be delimited by a wall. Advantageously, such a wall is transparent to ultraviolet radiation, so that the source, facing it, also in this case radiates the electromagnetic radiation curtain beam, 22, towards the outside, in a downward direction.

According to an advantageous embodiment of the present invention, the aforementioned sources 20 consist of excimer lamps, i.e., narrowband UV radiation emission sources, in the range indicated above, provided with high power, efficiency and easily available on the market. A choice of this type ensures high performance in terms of reducing the environmental viral and bacterial load, while safeguarding the limiting of production and maintenance costs.

According to the embodiment discussed, the source 20 in question is an excimer lamp of linear shape arranged longitudinally inside the main body 10. On the other hand, the use of other ultraviolet radiation sources of different shape and nature is not excluded. In the present case, alternative embodiments can include the use of high germicidal power UV LED modules or, still, laser beam sources.

In the depicted embodiment, in which the source 20 is not of a type such as to produce a collimated or otherwise oriented beam, the source 20 is housed inside containment means (not shown) comprising reflecting organs, 21, adapted to peripherally delimit the emitted radiation and direct it outwards in a certain direction so as to create the curtain shape of the electromagnetic radiation curtain beam 22. The association of the source 20 with structural and optical elements, such as the above-mentioned reflecting organs 21, is crucial for directing and delimiting the radiation. Thereby, in fact, the emission to the outside of a curtain electromagnetic radiation beam is ensured which, by virtue of the proximity of the sources 20 to the delivery organs 31, substantially overlaps the vertical laminar curtain-shaped air flow 33 fed by the latter.

Clearly, sources of a different nature from that illustrated can require different secondary optics. By way of example, the laser sources can preferably be associated with mirrors, such as galvanometric mirrors or rotating mirrors, while UV ray LED modules can preferably be associated with TIR lenses.

Preferably, the device according to the invention includes, associated with the source 20, sensor organs designed to detect bodies near the electromagnetic radiation curtain beam 22. Such sensor organs are responsible for interrupting the light emission if the UV barrier is crossed, in order to prevent the radiation from directly affecting people or objects. As a result, the already minimal risk associated with radiation exposure is almost eliminated.

A preferred, but not exclusive or limiting, embodiment of the present invention includes an auxiliary reflector assembly, 40, forming a separate unit from the main body 10 and located below the source 20 and at a certain distance therefrom. In particular, the auxiliary reflector assembly 40 extends in a longitudinal direction, parallel to the length of the main body 10. It is designed so that the relative reflecting surface is oriented towards the source 20, so that the radiation emitted, striking said reflecting surface, is returned to the source. The result is a curtain of UV rays with a high photon density, with an enhanced effect in terms of sanitising action.

Merely by way of example, the main body 10 has a main longitudinal extension direction of about 1 metre and is located about 1 metre away from said reflector system 40, arranged parallel to the main body, so that the resulting UV curtain has dimensions of 1×1 m. Its thickness can be negligible or even a few centimetres.

The reflective surfaces of the assembly 40 can be made of materials of various kinds, as long as they have properties of brightness, compactness and high reflectivity to ultraviolet radiation, such as aluminium or PTFE.

In the embodiment discussed, the auxiliary reflector assembly 40 forms a separate unit, separate from the main body 10; alternatively, according to an embodiment variant, it can be installed within a single support frame of substantially rectangular shape, which supports the main body 10 in the upper part and the assembly 40 in the lower part.

Figures 3, 4:
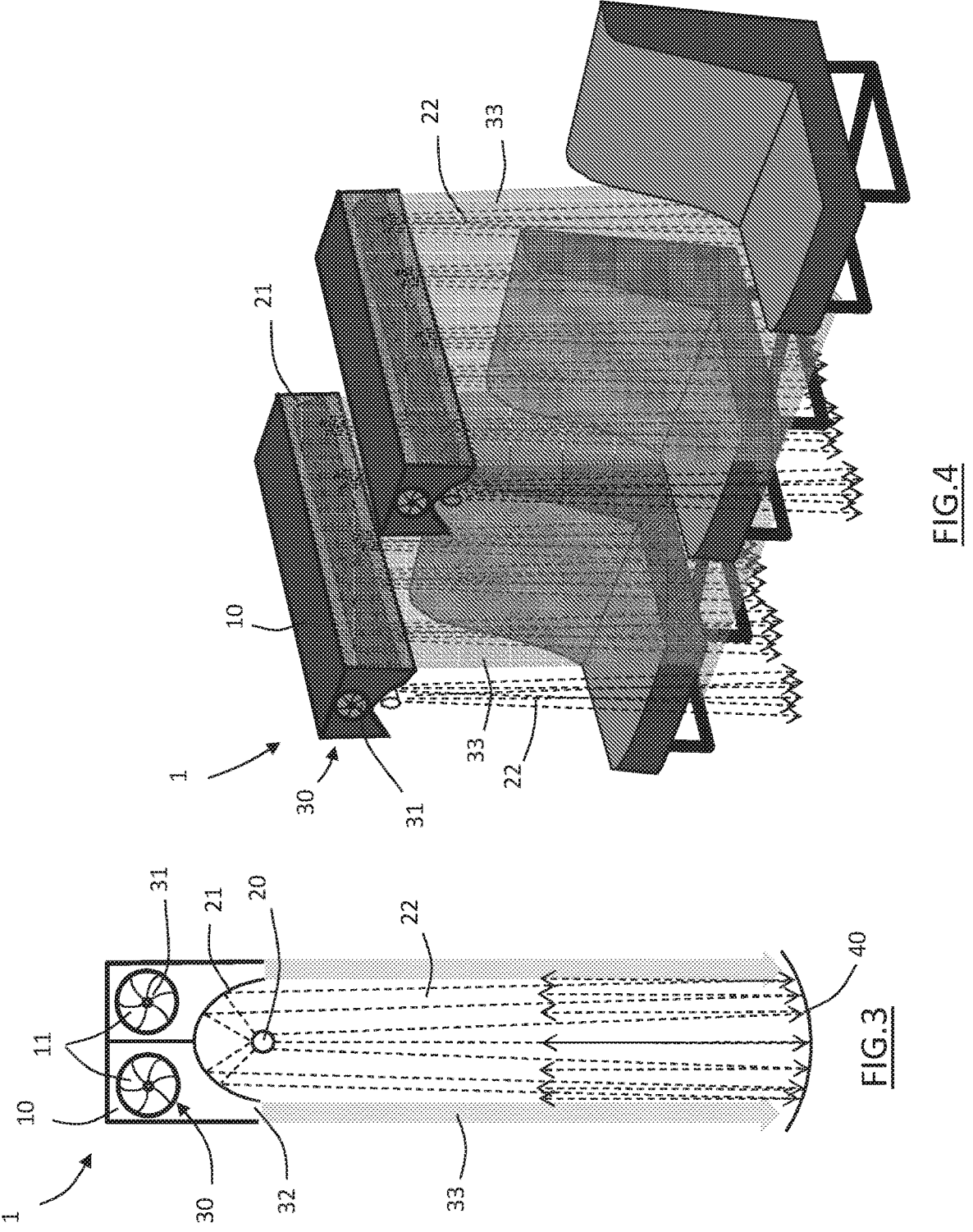
FIG. 3 is a schematic side view of an embodiment variant of the device in FIG. 1.
FIG. 4 is a schematic view of a possible application of an embodiment variant of the device according to the invention.

With reference to FIG. 3, an embodiment variant is depicted of which only the differences with respect to the embodiment described above will be discussed.

The variant in question has two adjacent openings formed in one of the side walls of the main body 10 and defining the air inlet. In detail, such a variant includes a double forced circulation and air channelling system, each preferably housed inside a separate chamber. Each channelling system identifies an air conveying path associated downstream with its delivery organs. Thereby, two opposite vertical laminar air flows are generated, directed downwards and identifying parallel surfaces of the same size. Notably, the two air flows in this configuration allow to further confine the ultraviolet radiation, the source 20 being located downstream of the dual channeling system in an intermediate position between the opposite delivery organs.

Referring to FIG. 4, a possible application of an embodiment variant includes the installation of a plurality of devices on the ceiling of a public room, such as a waiting room. In this case, the adjacent devices, each with the relative curtain-shaped air flow 33 emission associated with the electromagnetic radiation curtain beam 22, generate confined areas for housing a single seat. The variant in question does not include the reflector system separate from the main body 10 and described for the preferred embodiment, but this does not affect the achievement of the intended objects.

The device according to the invention fulfils the objects listed above by means of the synergistic effect of two principles, the use of a downwards vertical laminar air flow intended to direct polluting particles resident in the ambient air downwards and the generation of a continuous beam of ultraviolet radiation, in fact superimposed on said air flow, endowed with high germicidal power. The synergistic action of the superimposition of a curtain air flow with an ultraviolet radiation which is also curtain-shaped and substantially coplanar lies in the ability of the air flow to lengthen the residence time of the air particles passing through the action space of the ultraviolet radiation, thus greatly increasing the sanitation effectiveness of the device. Furthermore, as previously clarified, the wavelength of the radiation produced by the source 20 is advantageously chosen so as not to constitute any risk to humans, while offering high sterilising action. Nevertheless, in order to reduce any direct contact with persons and/or objects, the device is provided with sensors designed to interrupt the emission of radiation in the event of an approaching body crossing the barrier. It follows that the device according to the present invention meets the most stringent safety criteria in force for installations in populated environments.

According to another embodiment variant, further ultraviolet sources are included inside the main body 10 to radiate the air flow produced by the forced air circulation means 30 with a UV radiation which remains confined inside the main body 10, as is the case in devices of the known art. The aforesaid additional ultraviolet sources can be of the conventionally used type which emit radiation at a wavelength of around 254 nm since the UV rays emitted by the latter sanitise the air flow passing through the main body 10 of the device without being emitted outside and therefore without risk to humans.

In view of the foregoing, the device described is used in virtually every area in which the containment of airborne contagion is requested and, in this case, where it is desired to provide the spaces with separation barriers between stations or distinct areas. Given the small size and constructive simplicity, it is possible to envisage the installation thereof, for example, in waiting rooms, cinemas or public transport for the separation of adjacent seats and, similarly, in canteens, restaurants or even other typically crowded circumscribed environments. The constructive simplicity allows to propose the device according to the invention as a valid and more effective alternative to the widespread Plexiglass barriers, especially for the confinement of the operator in the operations of public necessity, such as pharmacies.

It is clear that the device thus conceived is susceptible to numerous modifications and variations. In practice, the construction details, the dimensions and the materials used can be extensively varied or replaced, without this entailing departing from the scope of protection as clarified by the following claims.

The invention claimed is:

1. An air sanitation device comprising a main body provided with one or more sources of emission of ultraviolet radiation and means for forced air circulation, wherein:

said sources for emitting ultraviolet radiation are such as to generate electromagnetic radiation in the wavelength range between 170 and 230 nm;

said air sanitation device comprises reflecting organs, arranged around said sources of emission of ultraviolet radiation, suitable for perimetrically confining and directing the radiation emitted by said sources in such a way that said device emits outwardly an electromagnetic radiation curtain beam, wherein the reflecting organs are disposed around the one or more sources and are adapted to peripherally delimit the emitted radiation and direct the emitted radiation outward in a predetermined direction so as to create a curtain shape of the electromagnetic radiation curtain beam, and said means for forced air circulation comprises channeling means configured to generate a substantially laminar, vertically oriented curtain-shaped air flow superimposed on or substantially adjacent to said electromagnetic radiation curtain beam, wherein said curtain-shaped airflow and said curtain beam are substantially coplanar and overlapping at an emission region adjacent an outlet of said channeling means so as to maintain airborne particles within the beam for an extended residence time.

2. The air sanitation device according to claim 1, comprising organs for controlling the temperature and the hygrometry of the outgoing air flow, intended to increase the temperature and humidify said outgoing curtain-shaped air flow.

3. The air sanitation device according to claim 1, comprising sensor organs for detecting bodies in the vicinity of said electromagnetic radiation curtain beam.

4. The air sanitation device according to claim 3, wherein said sensor organs deputed for detecting bodies in proximity of said electromagnetic radiation curtain beam induce the interruption of said electromagnetic radiation curtain beam in case said bodies or objects cross said electromagnetic radiation curtain beam.

5. The air sanitation device according to claim 1, comprising an auxiliary reflector assembly, placed externally to said main body and at a suitable distance therefrom, oriented towards said sources of emission of ultraviolet radiation in such an arrangement as to reflect and return to said sources the incident rays emitted by said sources.

6. The air sanitation device according to claim 1, wherein said means for forced air circulation comprise at least one fan housed in said main body.

7. The air sanitation device according to claim 1, wherein said means for forced air circulation comprise a compressed air container.

8. The air sanitation device according to claim 1, comprising further ultraviolet sources included within said main body for radiating the air flow produced by said means for forced air circulation with a UV radiation which remains confined within said main body.

9. An air sanitation device comprising a main body provided with one or more sources of emission of ultraviolet radiation and at least one fan or a compressed air container configured to generate forced air circulation, wherein:

said sources for emitting ultraviolet radiation are such as to generate electromagnetic radiation in the wavelength range between 170 and 230 nm;

said air sanitation device comprises reflecting organs, arranged around said sources of emission of ultraviolet radiation, suitable for perimetrically confining and directing the radiation emitted by said sources in such a way that said device emits outwardly an electromagnetic radiation curtain beam, wherein the reflecting organs are disposed around the one or more sources and are adapted to peripherally delimit the emitted radiation and direct the emitted radiation outward in a predetermined direction so as to create a curtain shape of the electromagnetic radiation curtain beam, and said at least one fan or compressed air container comprises a guide channel configured to generate a substantially laminar, vertically oriented curtain-shaped air flow superimposed on or substantially adjacent to said electromagnetic radiation curtain beam, wherein said curtain-shaped airflow and said curtain beam are substantially coplanar and overlapping at an emission region adjacent an outlet of said guide channel so as to maintain airborne particles within the beam for an extended residence time.

\* \* \* \* \*